United States Patent
Tang et al.

(10) Patent No.: US 11,332,430 B1
(45) Date of Patent: May 17, 2022

(54) PLEUROMULIN LAURIC ACID ESTER WITH ANTIBACTERIAL ACTIVITY AND A METHOD OF PREPARING THE SAME

(71) Applicants: Yonghong Tang, Xi'an (CN); Minghui Chang, Xi'an (CN); Huafeng Qi, Xi'an (CN); Peiyu Zhou, Xi'an (CN); Chengyuan Liang, Xi'an (CN); Xingke Ju, Xi'an (CN)

(72) Inventors: Yonghong Tang, Xi'an (CN); Minghui Chang, Xi'an (CN); Huafeng Qi, Xi'an (CN); Peiyu Zhou, Xi'an (CN); Chengyuan Liang, Xi'an (CN); Xingke Ju, Xi'an (CN)

(73) Assignee: XI'AN TAIKOMED PHARMACEUTICAL TECHNOLOGY CO., LTD., Shaanxi (CN)

(*) Notice: Subject to any disclaimer, the term of this patent is extended or adjusted under 35 U.S.C. 154(b) by 0 days.

(21) Appl. No.: 17/157,909

(22) Filed: Jan. 25, 2021

(51) Int. Cl.
  *C07C 67/08* (2006.01)
  *C07C 69/74* (2006.01)

(52) U.S. Cl.
  CPC .............. *C07C 67/08* (2013.01); *C07C 69/74* (2013.01)

(58) Field of Classification Search
  CPC .................................. C07C 67/08; C07C 69/74
  See application file for complete search history.

(56) References Cited

U.S. PATENT DOCUMENTS

RE43,390 E * 5/2012 Berry ...................... A61P 29/00
546/124

OTHER PUBLICATIONS

Helmut et al. (New Pleuromutilin Derivatives with Enhanced Antimicrobial Activity, II. Structure-Activity Correlations, The J. of Antibiotics, vol. XXIX No. 9, pp. 923-927, Published Sep. 1976) (Year: 1976).*

* cited by examiner

*Primary Examiner* — Jafar F Parsa
*Assistant Examiner* — Blaine G Doletski

(57) ABSTRACT

A compound having the following formula (I):

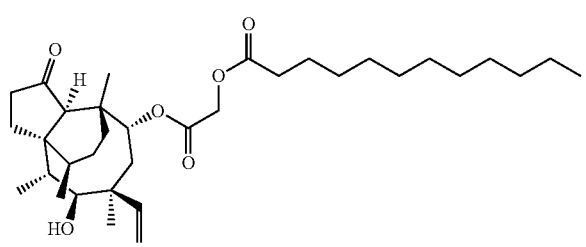

is disclosed. The methods of preparing the compound of formula (I) are also disclosed.

15 Claims, 4 Drawing Sheets

PLEUROMULIN LAURIC ACID ESTER WITH ANTIBACTERIAL ACTIVITY AND A METHOD OF PREPARING THE SAME

FIELD OF THE INVENTION

The present invention relates to the field of medicinal chemistry, and in particular, to a pleuromulin lauric acid ester with antibacterial activity and a method of preparing the same.

BACKGROUND OF THE INVENTION

In recent years, various types of drug-resistant bacteria have developed rapidly, which makes the drug resistance rate and infectious problems more serious. Multidrug-resistant bacteria infections (MDRB) are resistant to three or more types of antibacterial drugs. Common MDRBs include *Escherichia coli, Staphylococcus aureus, Acinetobacter baumannii, Pseudomonas aeruginosa*, and multidrug-resistant *Mycobacterium tuberculosis*. At present, multi-drug-resistant bacteria are an important source of infection, and the difficulty of controlling infection with antibacterial drugs is increasing. Therefore, it is urgent to solve the problem of bacterial resistance.

Pleuromulin (compound of formula (I)) is a broad-spectrum diterpene antibiotic produced by *Pleurotus mutilus*, and is the precursor of the semi-synthetic derivative of pleuromulin. Pleuromulin is a large family of antibiotics with good antibacterial activity, which can effectively inhibit most Gram-positive bacteria and some Gram-negative bacteria.

Lauric acid (compound of formula (II)) is a saturated fatty acid with 12 carbon atoms, with a slight laurel oil fragrance. The biggest effect of lauric acid is its antimicrobial ability, which can improve immunity. After consuming lauric acid, the antiviral ability is greatly improved, such as fighting the flu, fever, herpes and so on. Lauric acid can also relieve antibiotic resistance and reduce the risk of heart disease. For young women, a major benefit of lauric acid is skin care. Studies have shown that its skin care effect is much better than some well-known cosmetics.

In the present invention, pleuromulin is combined with lauric acid to obtain a pleuromulin lauric acid ester. Preliminary in vitro antibacterial activity experiment shows that the compound has excellent antibacterial activity and anti-drug-resistant bacteria activity.

SUMMARY OF THE INVENTION

In one embodiment, the present invention provides a compound having the following formula (I):

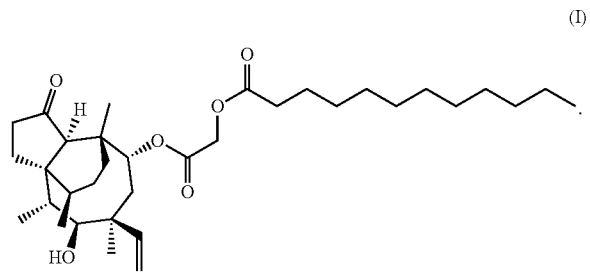 [SMILES: C=C[C@]1(C)C[C@@H](OC(=O)COC(=O)CCCCCCCCCCC)[C@]2(C)CC[C@@H](C)[C@@]3(CCC(=O)[C@@H]23)[C@@H](C)[C@@H]1O]

(I)

In another embodiment, the present invention provides a method of preparing the compound of formula (I). The method includes: reacting a compound of formula (II) with a compound of formula (III) to obtain the compound of formula (I):

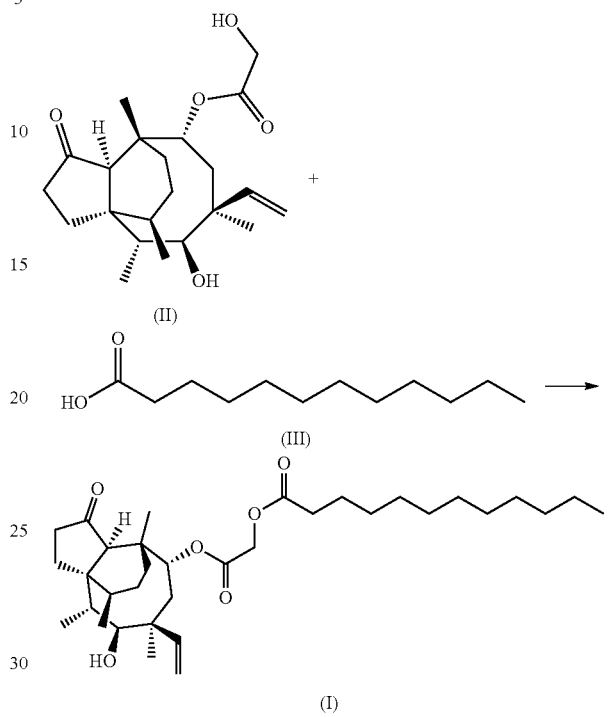

In another embodiment, the reaction of the compound of formula (II) with the compound of formula (III) comprises the following steps: placing the compound of formula (II) and the compound of formula (III), in a molar ratio of 1:1 to 1:1.3, in a reactor; adding an organic solvent and a catalytic amount of 4-dimethylamidopyridine (4-DMAP) under nitrogen atmosphere to obtain a reaction mixture; stirring the reaction mixture at 0° C. for five minutes and then adding N,N'-dicyclohexylcarbodiimide (DCC) to the reaction mixture; reacting the reaction mixture at 20-40° C. for 3 to 7 hours; extracting the reaction mixture with ethyl acetate to obtain a crude product; and purifying the crude product on a silica gel fresh chromatography column with petroleum ether and ethyl acetate with a ratio of 1:1 to 4:1 as an eluent to obtain the compound of formula (I).

In another embodiment, the organic solvent is toluene, dichloromethane or dimethylformamide (DMF).

In another embodiment, the organic solvent is dichloromethane.

In another embodiment, the molar ratio of the compound of formula (II) and the compound of formula (III) is 1:1.1.

In another embodiment, the reaction mixture is reacted at 20° C. for 5 hours.

In another embodiment, the eluent is petroleum ether: ethylacetate=1:1.

In another embodiment, the reaction of the compound of formula (II) with the compound of formula (III) comprises the following steps: placing the compound of formula (II), a catalyst, and an ionic liquid in a reactor under nitrogen atmosphere, the catalyst being 12-molybdosilicic acid hydrate ($H_6Mo_{12}O_{41}Si$); adding the compound of formula (III) to the reactor to form a reaction mixture; heating the reaction mixture at 20-50° C. for 4-8 hours; placing the reaction mixture in a separating funnel to separate a crude product; purifying the crude product by recrystallization in methanol to obtain the compound of formula (I); and recycling the ionic liquid.

In another embodiment, the ionic liquid is 1-octyl-3-methylimidazolium hexafluorophosphate ($C_{12}H_{23}F_6N_2P$), 1-hexyl-3-methylimidazolium tetrafluoroborate or 1-butyl-3-methylimidazolium tetrafluoroborate.

In another embodiment, the ionic liquid is 1-octyl-3-methylimidazolium hexafluorophosphate ($C_{12}H_{23}F_6N_2P$).

In another embodiment, the compound of formula (II) and the compound (III) have a molar ratio of 1:1 to 1:1.3.

In another embodiment, the molar ratio of the compound of formula (II) and the compound of formula (III) is 1:1.1.

In another embodiment, the reaction mixture is heated at 30° C.

In another embodiment, the reaction mixture is heated for 6 hours.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings.

DETAILED DESCRIPTION OF THE ILLUSTRATED EMBODIMENTS

Reference will now be made in detail to embodiments of the present invention, example of which is illustrated in the accompanying drawings. The following examples illustrate the present invention, but the present invention is not limited to the following examples.

Example 1

Preparation of Compound 2-(((3aS,4R,5S,6S,8R,9R,9aR,12R)-5-hydroxy-4,6,9,12-tetramethyl-1-oxo-6-vinyldecahydro-3a,9-propanocyclopenta[8]annulen-8-yl)oxy)-2-oxoethyl Dodecanoate (Compound of Formula (I))

In a 100 mL three-necked flask, 378.5 mg (1.00 mmol) of pleuromulin and 3.7 mg (0.03 mmol) 4-DMAP of were dissolved in 20 mL of dichloromethane under nitrogen atmosphere. 220.4 mg (1.10 mmol) of lauric acid was dissolved in 15 mL of dichloromethane, and added dropwise to the reaction mixture by a separatory funnel. After the completion of the dropwise addition, the reaction was stirred for 5 minutes at 0° C., and 206.3 mg (1.00 mmol) of coupling agent DCC was added. The reaction mixture was removed from the ice bath, and stirred at 20° C. for 5 hours. Thin layer chromatography was used to track the reaction to completion. The reaction mixture was washed with water, extracted with ethyl acetate, dried and concentrated to give a crude product. The crude product was purified by silica gel column chromatography, with petroleum ether:ethyl acetate=1:1 as eluent. The eluent containing the product was combined, concentrated under reduced pressure and dried to obtain 485.6 mg of the titled compound, a yield of 71.58%.

Figure 4:
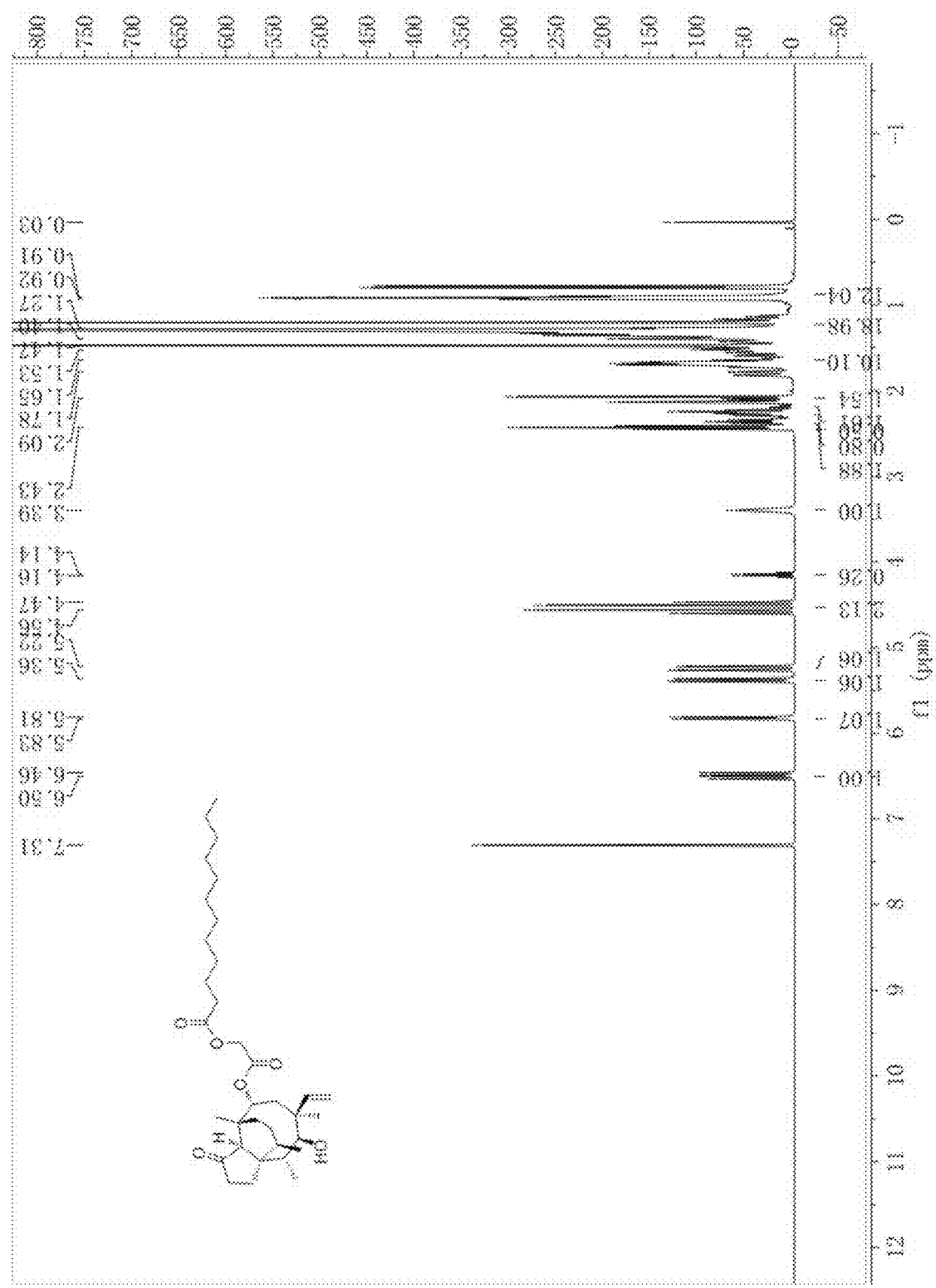
FIG. 4 is the $^1$H-NMR spectrum of the pleuromulin lauric acid.
Figure 5:
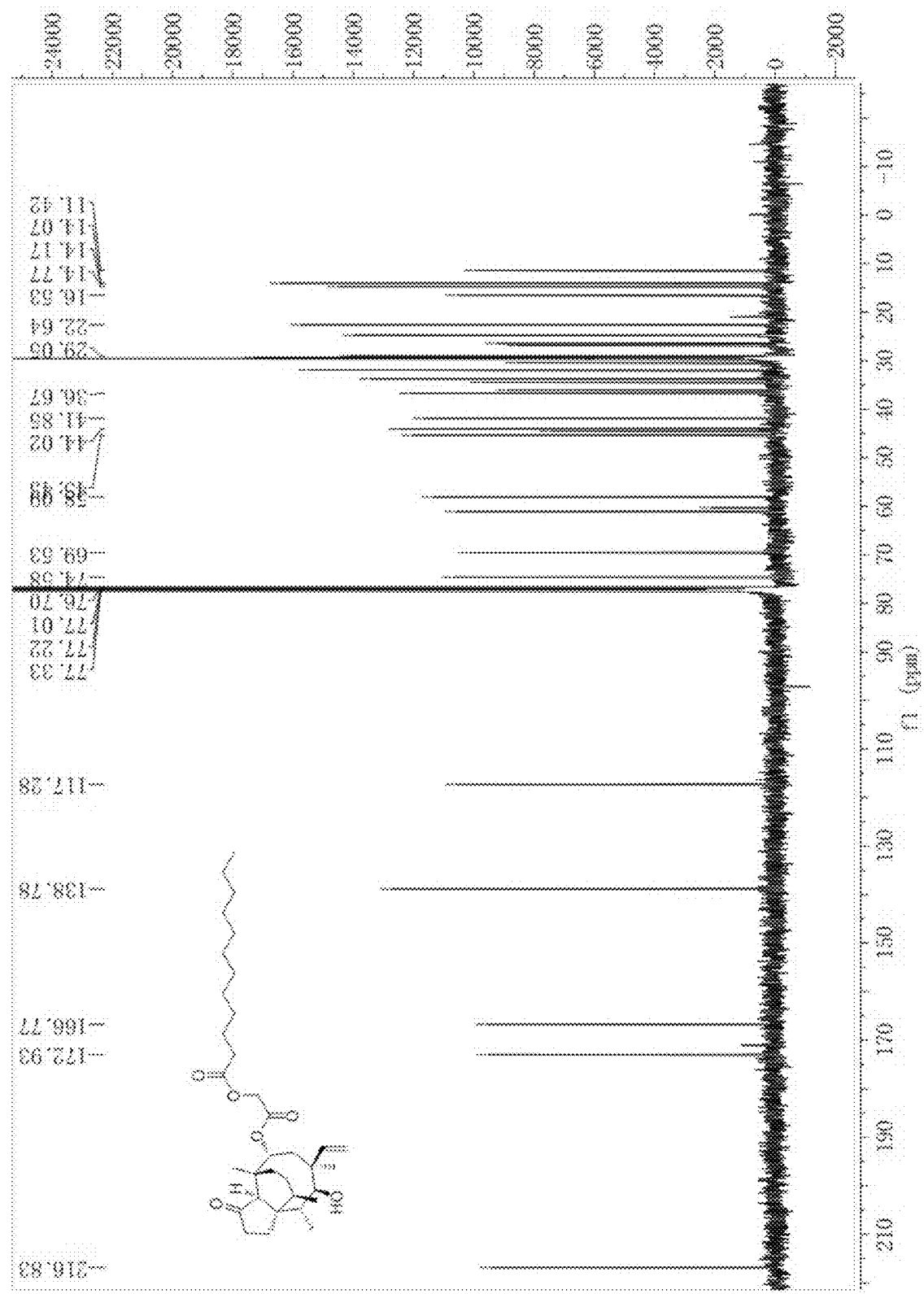
FIG. 5 is the $^{13}$C-NMR spectrum of the pleuromulin lauric acid.

$^1$H-NMR (400 MHz, chloroform-d) δ (ppm): 6.50 (1H, m), 5.83 (1H, d), 5.36 (1H, d), 5.22 (1H, d), 4.60 (2H, m), 3.39 (1H, s), 2.43 (1H, d), 2.38 (2H, t), 2.29 (1H, s), 2.26 (2H, t), 2.13 (2H, t), 1.82-1.47 (10H, m), 1.33-1.14 (19H, m), 0.92-0.78 (12H, m). The $^1$H-NMR spectrum is shown in FIG. 4. $^{13}$C-NMR (400 MHz, chloroform-d) δ (ppm): 216.8, 172.9, 166.8, 138.8, 117.3, 74.6, 69.5, 61.1, 60.3, 58.1, 45.4, 44.6, 44.0, 41.9, 36.7, 36.0, 33.7, 31.9, 29.4, 29.1, 26.8, 26.4, 24.8, 24.7, 22.6, 16.5, 14.8, 14.2, 14.1, 11.4. The $^{13}$C-NMR is shown in FIG. 5.

Example 2

Preparation of Compound 2-(((3aS,4R,5S,6S,8R,9R,9aR,12R)-5-hydroxy-4,6,9,12-tetramethyl-1-oxo-6-vinyldecahydro-3a,9-propanocyclopenta[8]annulen-8-yl)oxy)-2-oxoethyl Dodecanoate In a 100 mL three-necked flask, 378.5 mg (1.00 mmol) of pleuromulin and 3.7 mg (0.03 mmol) 4-DMAP of were dissolved in 20 mL of dichloromethane under nitrogen atmosphere. 240.4 mg (1.20 mmol) of lauric acid was dissolved in 15 mL of dichloromethane, and added dropwise to the reaction mixture by a separatory funnel. After the completion of the dropwise addition, the reaction was stirred for 5 minutes at 0° C., and 206.3 mg (1.00 mmol) of coupling agent DCC was added. The reaction mixture was removed from the ice bath, and stirred at 40° C. for 3 hours. Thin layer chromatography was used to track the reaction to completion. The reaction mixture was washed with water, extracted with ethyl acetate, dried and concentrated to give a crude product. The crude product was purified by silica gel column chromatography, with petroleum ether:ethyl acetate=1:1 as eluent. The eluent containing the product was combined, concentrated under reduced pressure and dried to obtain 371.8 mg of the titled compound, a yield of 66.34%.

Example 3

Preparation of Compound 2-(((3aS,4R,5S,6S,8R,9R,9aR,12R)-5-hydroxy-4,6,9,12-tetramethyl-1-oxo-6-vinyldecahydro-3a,9-propanocyclopenta[8]annulen-8-yl)oxy)-2-oxoethyl Dodecanoate In a 100 mL three-necked flask, 378.5 mg (1.00 mmol) of pleuromulin and 3.7 mg (0.03 mmol) 4-DMAP of were dissolved in 20 mL of dichloromethane under nitrogen atmosphere. 260.4 mg (1.30 mmol) of lauric acid was dissolved in 15 mL of dichloromethane, and added dropwise to the reaction mixture by a separatory funnel. After the completion of the dropwise addition, the reaction was stirred for 5 minutes at 0° C., and 206.3 mg (1.00 mmol) of coupling agent DCC was added. The reaction mixture was removed from the ice bath, and stirred at 30° C. for 6 hours. Thin layer chromatography was used to track the reaction to completion. The reaction mixture was washed with water, extracted with ethyl acetate, dried and concentrated to give a crude product. The crude product was purified by silica gel column chromatography, with petroleum ether:ethyl acetate=1:1 as eluent. The eluent containing the product was combined, concentrated under reduced pressure and dried to obtain 368.7 mg of the titled compound, a yield of 65.79%.

Example 4

Preparation of Compound 2-(((3aS,4R,5S,6S,8R,9R, 9aR,12R)-5-hydroxy-4,6,9,12-tetramethyl-1-oxo-6-vinyldecahydro-3a,9-propanocyclopenta[8]annulen-8-yl)oxy)-2-oxoethyl Dodecanoate In a 100 mL three-necked flask, 378.5 mg (1.00 mmol) of pleuromulin and 3.7 mg (0.03 mmol) 4-DMAP of were dissolved in 20 mL of dichloromethane under nitrogen atmosphere. 220.4 mg (1.10 mmol) of lauric acid was dissolved in 15 mL of dichloromethane, and added dropwise to the reaction mixture by a separatory funnel. After the completion of the dropwise addition, the reaction was stirred for 5 minutes at 0° C., and 206.3 mg (1.00 mmol) of coupling agent DCC was added. The reaction mixture was removed from the ice bath, and stirred at 20° C. for 5 hours. Thin layer chromatography was used to track the reaction to completion. The reaction mixture was washed with water, extracted with ethyl acetate, dried and concentrated to give a crude product. The crude product was purified by silica gel column chromatography, with petroleum ether:ethyl acetate=1:1 as eluent. The eluent containing the product was combined, concentrated under reduced pressure and dried to obtain 360.8 mg of the titled compound, a yield of 64.38%.

Example 5

Preparation of Compound 2-(((3aS,4R,5S,6S,8R,9R, 9aR,12R)-5-hydroxy-4,6,9,12-tetramethyl-1-oxo-6-vinyldecahydro-3a,9-propanocyclopenta[8]annulen-8-yl)oxy)-2-oxoethyl Dodecanoate In a 100 mL three-necked flask, 378.5 mg (1.00 mmol) of pleuromulin and 3.7 mg (0.03 mmol) 4-DMAP of were dissolved in 20 mL of toluene under nitrogen atmosphere. 240.4 mg (1.20 mmol) of lauric acid was dissolved in 15 mL of toluene, and added dropwise to the reaction mixture by a separatory funnel. After the completion of the dropwise addition, the reaction was stirred for 5 minutes at 0° C., and 206.3 mg (1.00 mmol) of coupling agent DCC was added. The reaction mixture was removed from the ice bath, and stirred at 40° C. for 6 hours. Thin layer chromatography was used to track the reaction to completion. The reaction mixture was washed with water, extracted with ethyl acetate, dried and concentrated to give a crude product. The crude product was purified by silica gel column chromatography, with petroleum ether:ethyl acetate=1:1 as eluent. The eluent containing the product was combined, concentrated under reduced pressure and dried to obtain 361.1 mg of the titled compound, a yield of 64.43%.

Example 6

Preparation of Compound 2-(((3aS,4R,5S,6S,8R,9R, 9aR,12R)-5-hydroxy-4,6,9,12-tetramethyl-1-oxo-6-vinyldecahydro-3a,9-propanocyclopenta[8]annulen-8-yl)oxy)-2-oxoethyl Dodecanoate In a 100 mL three-necked flask, 378.5 mg (1.00 mmol) of pleuromulin and 3.7 mg (0.03 mmol) 4-DMAP of were dissolved in 20 mL of toluene under nitrogen atmosphere. 260.4 mg (1.30 mmol) of lauric acid was dissolved in 15 mL of toluene, and added dropwise to the reaction mixture by a separatory funnel. After the completion of the dropwise addition, the reaction was stirred for 5 minutes at 0° C., and 206.3 mg (1.00 mmol) of coupling agent DCC was added. The reaction mixture was removed from the ice bath, and stirred at 30° C. for 5 hours. Thin layer chromatography was used to track the reaction to completion. The reaction mixture was washed with water, extracted with ethyl acetate, dried and concentrated to give a crude product. The crude product was purified by silica gel column chromatography, with petroleum ether:ethyl acetate=1:1 as eluent. The eluent containing the product was combined, concentrated under reduced pressure and dried to obtain 355.7 mg of the titled compound, a yield of 63.47%.

Example 7

Preparation of Compound 2-(((3aS,4R,5S,6S,8R,9R, 9aR,12R)-5-hydroxy-4,6,9,12-tetramethyl-1-oxo-6-vinyldecahydro-3a,9-propanocyclopenta[8]annulen-8-yl)oxy)-2-oxoethyl Dodecanoate In a 100 mL three-necked flask, 378.5 mg (1.00 mmol) of pleuromulin and 3.7 mg (0.03 mmol) 4-DMAP of were dissolved in 20 mL of DMF under nitrogen atmosphere. 240.4 mg (1.20 mmol) of lauric acid was dissolved in 15 mL of DMF, and added dropwise to the reaction mixture by a separatory funnel. After the completion of the dropwise addition, the reaction was stirred for 5 minutes at 0° C., and 206.3 mg (1.00 mmol) of coupling agent DCC was added. The reaction mixture was removed from the ice bath, and stirred at 20° C. for 5 hours. Thin layer chromatography was used to track the reaction to completion. The reaction mixture was washed with water, extracted with ethyl acetate, dried and concentrated to give a crude product. The crude product was purified by silica gel column chromatography, with petroleum ether:ethyl acetate=1:1 as eluent. The eluent containing the product was combined, concentrated under reduced pressure and dried to obtain 373.1 mg of the titled compound, a yield of 66.58%.

Example 8

Preparation of Compound 2-(((3aS,4R,5S,6S,8R,9R, 9aR,12R)-5-hydroxy-4,6,9,12-tetramethyl-1-oxo-6-vinyldecahydro-3a,9-propanocyclopenta[8]annulen-8-yl)oxy)-2-oxoethyl Dodecanoate In a 100 mL three-necked flask, 378.5 mg (1.00 mmol) of pleuromulin and 3.7 mg (0.03 mmol) 4-DMAP of were dissolved in 20 mL of DMF under nitrogen atmosphere. 240.4 mg (1.20 mmol) of lauric acid was dissolved in 15 mL of DMF, and added dropwise to the reaction mixture by a separatory funnel. After the completion of the dropwise addition, the reaction was stirred for 5 minutes at 0° C., and 206.3 mg (1.00 mmol) of coupling agent DCC was added. The reaction mixture was removed from the ice bath, and stirred at 20° C. for 5 hours. Thin layer chromatography was used to track the reaction to completion. The reaction mixture was washed with water, extracted with ethyl acetate, dried and concentrated to give a crude product. The crude product was purified by silica gel column chromatography, with petroleum ether:ethyl acetate=2:1 as eluent. The eluent containing the product was combined, concentrated under reduced pressure and dried to obtain 353.1 mg of the titled compound, a yield of 63.01%.

Example 9

Preparation of Compound 2-(((3aS,4R,5S,6S,8R,9R,9aR,12R)-5-hydroxy-4,6,9,12-tetramethyl-1-oxo-6-vinyldecahydro-3a,9-propanocyclopenta[8]annulen-8-yl)oxy)-2-oxoethyl Dodecanoate In a 100 mL three-necked flask, 378.5 mg (1.00 mmol) of pleuromulin and 3.7 mg (0.03 mmol) 4-DMAP of were dissolved in 20 mL of DMF under nitrogen atmosphere. 260.4 mg (1.30 mmol) of lauric acid was dissolved in 15 mL of DMF, and added dropwise to the reaction mixture by a separatory funnel. After the completion of the dropwise addition, the reaction was stirred for 5 minutes at 0° C., and 206.3 mg (1.00 mmol) of coupling agent DCC was added. The reaction mixture was removed from the ice bath, and stirred at 40° C. for 3 hours. Thin layer chromatography was used to track the reaction to completion. The reaction mixture was washed with water, extracted with ethyl acetate, dried and concentrated to give a crude product. The crude product was purified by silica gel column chromatography, with petroleum ether:ethyl acetate=3:1 as eluent. The eluent containing the product was combined, concentrated under reduced pressure and dried to obtain 340.3 mg of the titled compound, a yield of 60.72%.

Example 10

Preparation of Compound 2-(((3aS,4R,5S,6S,8R,9R,9aR,12R)-5-hydroxy-4,6,9,12-tetramethyl-1-oxo-6-vinyldecahydro-3a,9-propanocyclopenta[8]annulen-8-yl)oxy)-2-oxoethyl Dodecanoate In a 100 mL three-necked flask, 378.5 mg (1.00 mmol) of pleuromulin and 3.7 mg (0.03 mmol) 4-DMAP of were dissolved in 20 mL of dichloromethane under nitrogen atmosphere. 250.4 mg (1.25 mmol) of lauric acid was dissolved in 15 mL of dichloromethane, and added dropwise to the reaction mixture by a separatory funnel. After the completion of the dropwise addition, the reaction was stirred for 5 minutes at 0° C., and 206.3 mg (1.00 mmol) of coupling agent DCC was added. The reaction mixture was removed from the ice bath, and stirred at 35° C. for 5 hours. Thin layer chromatography was used to track the reaction to completion. The reaction mixture was washed with water, extracted with ethyl acetate, dried and concentrated to give a crude product. The crude product was purified by silica gel column chromatography, with petroleum ether:ethyl acetate=4:1 as eluent. The eluent containing the product was combined, concentrated under reduced pressure and dried to obtain 357.5 mg of the titled compound, a yield of 63.79%.

Example 11

Preparation of Compound 2-(((3aS,4R,5S,6S,8R,9R,9aR,12R)-5-hydroxy-4,6,9,12-tetramethyl-1-oxo-6-vinyldecahydro-3a,9-propanocyclopenta[8]annulen-8-yl)oxy)-2-oxoethyl Dodecanoate In a 100 mL three-necked flask, 378.5 mg (1.00 mmol) of pleuromulin and 3.7 mg (0.03 mmol) 4-DMAP of were dissolved in 20 mL of dichloromethane under nitrogen atmosphere. 220.4 mg (1.10 mmol) of lauric acid was dissolved in 15 mL of dichloromethane, and added dropwise to the reaction mixture by a separatory funnel. After the completion of the dropwise addition, the reaction was stirred for 5 minutes at 0° C., and 206.3 mg (1.00 mmol) of coupling agent DCC was added. The reaction mixture was removed from the ice bath, and stirred at 25° C. for 5 hours. Thin layer chromatography was used to track the reaction to completion. The reaction mixture was washed with water, extracted with ethyl acetate, dried and concentrated to give a crude product. The crude product was purified by silica gel column chromatography, with petroleum ether:ethyl acetate=3:1 as eluent. The eluent containing the product was combined, concentrated under reduced pressure and dried to obtain 352.2 mg of the titled compound, a yield of 62.85%.

Example 12

Preparation of Compound 2-(((3aS,4R,5S,6S,8R,9R,9aR,12R)-5-hydroxy-4,6,9,12-tetramethyl-1-oxo-6-vinyldecahydro-3a,9-propanocyclopenta[8]annulen-8-yl)oxy)-2-oxoethyl Dodecanoate In a 250 mL three-necked flask, 378.5 mg (1.00 mmol) of pleuromulin, 220.4 mg (1.10 mmol) of lauric acid and 20.3 mg (0.011 mmol) silicomolybdic acid were dissolved in 100 mL of 1-octyl-3-methylimidazolium hexafluorophosphate under nitrogen atmosphere. After full dissolution, the temperature of the reaction mixture was raised to 30° C. and the reaction was carried out for 6 hours. Thin layer chromatography was used to track the reaction to completion, heating was stopped, and the protective device was removed. The reaction mixture system was allowed to separate into layers to give a crude product. 1-Octyl-3-methylimidazolium hexafluorophosphate was recycled. The crude product was recrystallized with 50 mL methanol and dried to obtain 488.2 mg of the titled compound, a yield of 87.11%.

Example 13

Preparation of Compound 2-(((3aS,4R,5S,6S,8R,9R,9aR,12R)-5-hydroxy-4,6,9,12-tetramethyl-1-oxo-6-vinyldecahydro-3a,9-propanocyclopenta[8]annulen-8-yl)oxy)-2-oxoethyl Dodecanoate In a 250 mL three-necked flask, 378.5 mg (1.00 mmol) of pleuromulin, 220.4 mg (1.10 mmol) of lauric acid and 20.3 mg (0.011 mmol) silicomolybdic acid were dissolved in 100 mL of 1-butyl-3-methylimidazolium tetrafluoroborate under nitrogen atmosphere. After full dissolution, the temperature of the reaction mixture was raised to 30° C. and the reaction was carried out for 6 hours. Thin layer chromatography was used to track the reaction to completion, heating was stopped, and the protective device was removed. The reaction mixture system was allowed to separate into layers to give a crude product. 1-Butyl-3-methylimidazolium tetrafluoroborate was recycled. The crude product was recrystallized with 50 mL methanol and dried to obtain 466.5 mg of the titled compound, a yield of 83.24%.

Example 14

Preparation of Compound 2-(((3aS,4R,5S,6S,8R,9R,9aR,12R)-5-hydroxy-4,6,9,12-tetramethyl-1-oxo-6-vinyldecahydro-3a,9-propanocyclopenta[8]annulen-8-yl)oxy)-2-oxoethyl Dodecanoate In a 250 mL three-necked flask, 378.5 mg (1.00 mmol) of pleuromulin, 220.4 mg (1.10 mmol) of lauric acid and 20.3 mg (0.011 mmol) silicomolybdic acid were dissolved in 100 mL of 1-hexyl-3-methylimidazolium tetrafluoroborate under nitrogen atmosphere. After full dissolution, the temperature of the reaction mixture was raised to 40° C. and the reaction was carried out for 5 hours. Thin layer chromatography was used to track the reaction to completion, heating was stopped, and the protective device was removed. The reaction mixture system was allowed to separate into layers to give a crude product. 1-Hexyl-3-methylimidazolium tetrafluoroborate was recycled. The crude product was recrystallized with 50 mL methanol and dried to obtain 473.6 mg of the titled compound, a yield of 84.51%.

Example 15

Preparation of Compound 2-(((3aS,4R,5S,6S,8R,9R, 9aR,12R)-5-hydroxy-4,6,9,12-tetramethyl-1-oxo-6-vinyldecahydro-3a,9-propanocyclopenta[8]annulen-8-yl)oxy)-2-oxoethyl Dodecanoate In a 250 mL three-necked flask, 378.5 mg (1.00 mmol) of pleuromulin, 220.4 mg (1.10 mmol) of lauric acid and 20.3 mg (0.011 mmol) silicomolybdic acid were dissolved in 100 mL of 1-octyl-3-methylimidazolium hexafluorophosphate. After full dissolution, the temperature of the reaction mixture was raised to 20° C. and the reaction was carried out for 6 hours. Thin layer chromatography was used to track the reaction to completion, heating was stopped, and the protective device was removed. The reaction mixture system was allowed to separate into layers to give a crude product. 1-Octyl-3-methylimidazolium hexafluorophosphate was recycled. The crude product was recrystallized with 50 mL methanol and dried to obtain 478.9 mg of the titled compound, a yield of 85.45%.

Example 16

Antibacterial Activity Test of the Compounds of the Invention

The antimicrobial efficacy was determined by a paper diffusion method drug sensitivity test.

Experimental strains: multi-resistant *Staphylococcus aureus* 171, multi-resistant *Staphylococcus aureus* 575, multi-resistant *Staphylococcus aureus* 596. The experimental strain was identified by Huashan Hospital Affiliated to Fudan University (Institute of Antibiotic of Fudan University).

Drug sensitive paper: The drug sensitive paper is a special drug sensitive paper with a diameter of 6.35 mm and a water absorption of 0.02 mL. The control was vancomycin (30 μg/tablet); the test compounds were pleuromulin (30 μg/tablet), lauric acid (30 μg/tablet) and pleuromulin lauric acid ester (30 μg/tablet).

Reagents: LB agar medium, LA broth medium, 0.5% DMSO solution.

Equipment: Ultra-clean workbench, high-pressure sterilization pot, gas bath constant temperature shaking incubator.

Preparation of Bacterial Suspension:

The experimental strains were inoculated in non-selective medium and placed in air at 37° C. for 24 h. A single colony that grows well and inoculate it into broth medium was incubate at 35° C.±2° C. for 6 hours, and LA broth medium was used to calibrate the concentration of the bacterial solution to 0.5 Mie turbidimetric tube (1.5×10$^8$ CFU/mL). A bacterial suspension was obtained.

Paper Diffusion Method Drug Sensitivity Test:

LB dry powder was weighed, sterilized at 103.4 Kpa, 121.3° C. high-pressure steam for 15 min, and then placed it in a 40° C.-50° C. water bath. A sterile empty plate (inner diameter 9 cm) was placed on the surface of the ultra-clean table water table, and LB dry powder was poured to the plate. The thickness of each plate was 3 mm to 4 mm. After the plate was cooled at room temperature, it was stored in the refrigerator at 2° C.-8° C. A sterile cotton swab was used to dip the bacterial solution and ti evenly coat the surface of the LB plate 3 times. After inoculation of the bacterial suspension, the LB plate was dried at room temperature for 3 min to 5 min. Sterile forceps were used to closely attach the antibacterial drug paper to the dish. The dish was put upside down and placed in a 37° C. incubator for 24 h. The results were observed by measuring the diameter. Taking 0.5% DMSO solution as a negative control, the antibacterial activity is expressed by the diameter of the inhibition zone. The inhibition zone ≥17 mm, sensitive; the inhibition zone of 15 mm-16 mm, intermediary; the inhibition zone ≤14 mm, drug resistance.

Figure 1:
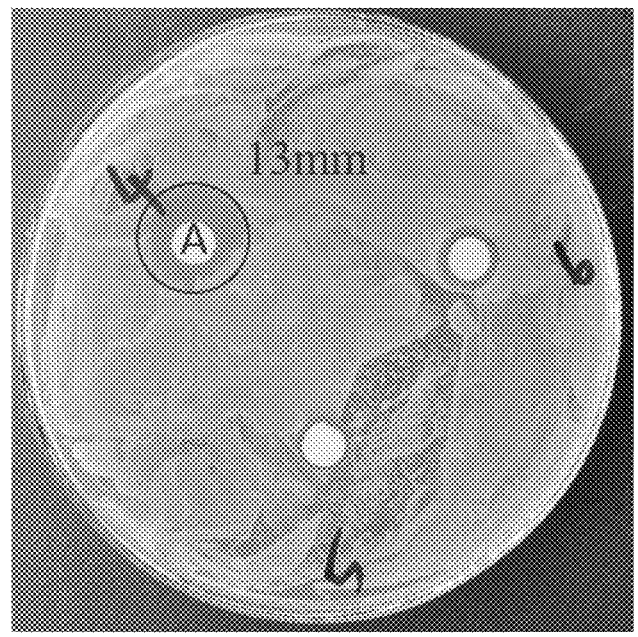
FIG. 1 shows the in vitro antibacterial activity of the pleuromulin lauric acid ester against drug-resistant bacteria MRSA 206.
Figure 2:
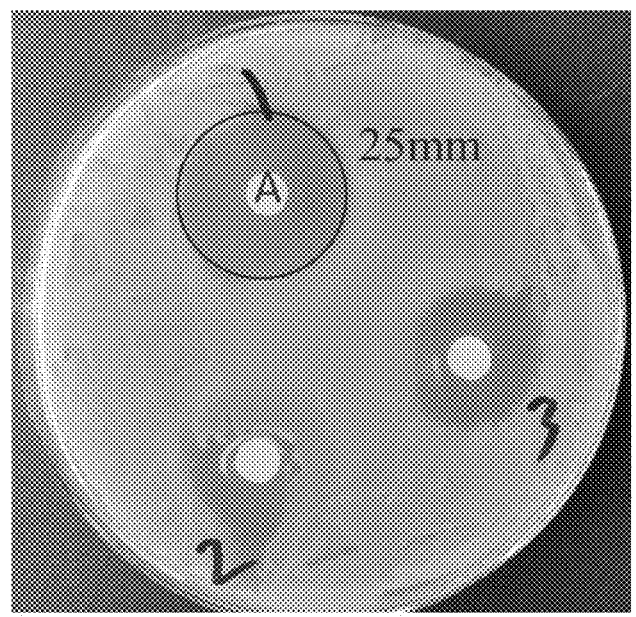
FIG. 2 shows the in vitro antibacterial activity of the pleuromulin lauric acid ester against drug-resistant bacteria MRSA 575.
Figure 3:
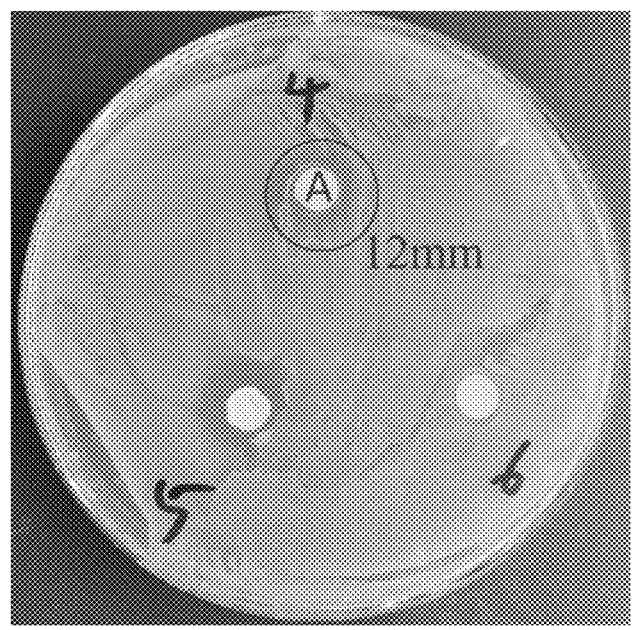
FIG. 3 shows the in vitro antibacterial activity of the pleuromulin lauric acid ester against drug-resistant bacteria MRSA 596.

In FIGS. 1-3, pleuromulin lauric acid ester is represented by the letter A. FIG. 1 shows the antibacterial effect of pleuromulin lauric acid ester on MRSA-206. FIG. 2 shows the antibacterial effect of pleuromulin lauric acid ester on MRSA-575. FIG. 3 shows the antibacterial effect of pleuromulin lauric acid ester on MRSA-596. The results are shown in Table 1.

TABLE 1

Experimental results of the zone of inhibition

| Compounds | Zone of inhibition/mm Strain | | |
|---|---|---|---|
| | MRSA-206 | MRSA-575 | MRSA-596 |
| 0.5% DMSO | 0 | 0 | 0 |
| Vancomycin | 15 | 17 | 23 |
| Pleuromulin | 0 | 0 | 0 |
| Laurie acid | 0 | 0 | 0 |
| Pleuromulinlauric acid ester | 13 | 25 | 12 |

FIGS. 1-3 and Table 1 show that pleuromutilin and lauric acid have no inhibitory effect on drug-resistant bacteria. Pleuromulin lauric acid derivative have strong inhibitory effects on multi-drug resistant *Staphylococcus aureus* 206, 575, 596, and the diameter of bacteriostatic zone against multidrug resistant *Staphylococcus aureus* 575 was up to 25 mm. In summary, the pleuromulin lauric acid derivative of the present invention can be used as an antibacterial drug candidate for multi-drug resistant *Staphylococcus aureus*, and further preclinical studies will be conducted.

What is claimed is:

1. A compound having the following formula (I):

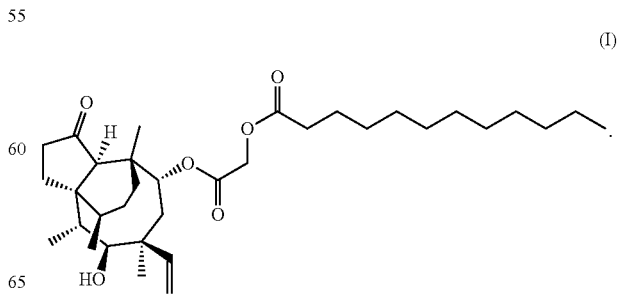

2. A method of preparing the compound of formula (I) of claim 1, comprising:
reacting a compound of formula (II) with a compound of formula (III) to obtain the compound of formula (I):

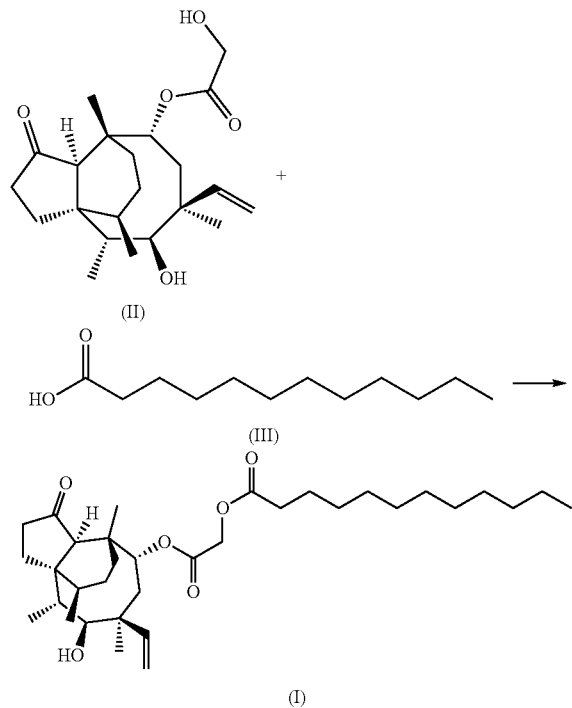

3. The method of claim 2, wherein the reaction of the compound of formula (II) with the compound of formula (III) comprises the following steps:
placing the compound of formula (II) and the compound of formula (III), in a molar ratio of 1:1 to 1:1.3, in a reactor;
adding an organic solvent and a catalytic amount of 4-dimethylamidopyridine (4-DMAP) under nitrogen atmosphere to obtain a reaction mixture;
stirring the reaction mixture at 0° C. for five minutes and then adding N,N'-dicyclohexylcarbodiimide (DCC) to the reaction mixture;
reacting the reaction mixture at 20-40° C. for 3 to 7 hours;
extracting the reaction mixture with ethyl acetate to obtain a crude product; and
purifying the crude product on a silica gel fresh chromatography column with petroleum ether and ethyl acetate with a ratio of 1:1 to 4:1 as an eluent to obtain the compound of formula (I).

4. The method of claim 3, wherein the organic solvent is toluene, dichloromethane or dimethylformamide (DMF).

5. The method of claim 4, wherein the organic solvent is dichloromethane.

6. The method of claim 3, wherein the molar ratio of the compound of formula (II) and the compound of formula (III) is 1:1.1.

7. The method of claim 3, wherein the reaction mixture is reacted at 20° C. for 5 hours.

8. The method of claim 3, wherein the eluent is petroleum ether:ethyl acetate=1:1.

9. The method of claim 2, wherein the reaction of the compound of formula (II) with the compound of formula (III) comprises the following steps:
placing the compound of formula (II), a catalyst, and an ionic liquid in a reactor under nitrogen atmosphere, the catalyst being 12-molybdosilicic acid hydrate ($H_6Mo_{12}O_{41}Si$);
adding the compound of formula (III) to the reactor to form a reaction mixture;
heating the reaction mixture at 20-50° C. for 4-8 hours;
placing the reaction mixture in a separating funnel to separate a crude product;
purifying the crude product by recrystallization in methanol to obtain the compound of formula (I); and
recycling the ionic liquid.

10. The method of claim 9, wherein the ionic liquid is 1-octyl-3-methylimidazolium hexafluorophosphate ($C_{12}H_{23}F_6N_2P$), 1-hexyl-3-methylimidazolium tetrafluoroborate or 1-butyl-3-methylimidazolium tetrafluoroborate.

11. The method of claim 10, wherein the ionic liquid is 1-octyl-3-methylimidazolium hexafluorophosphate ($C_{12}H_{23}F_6N_2P$).

12. The method of claim 10, wherein the compound of formula (II) and the compound (III) have a molar ratio of 1:1 to 1:1.3.

13. The method of claim 11, wherein the molar ratio of the compound of formula (II) and the compound of formula (III) is 1:1.1.

14. The method of claim 10, wherein the reaction mixture is heated at 30° C.

15. The method of claim 10, wherein the reaction mixture is heated for 6 hours.

* * * * *